Sept. 23, 1958 H. D. DOUGHERTY Plant Pat. 1,753
NECTARINE TREE
Filed Jan. 14, 1958
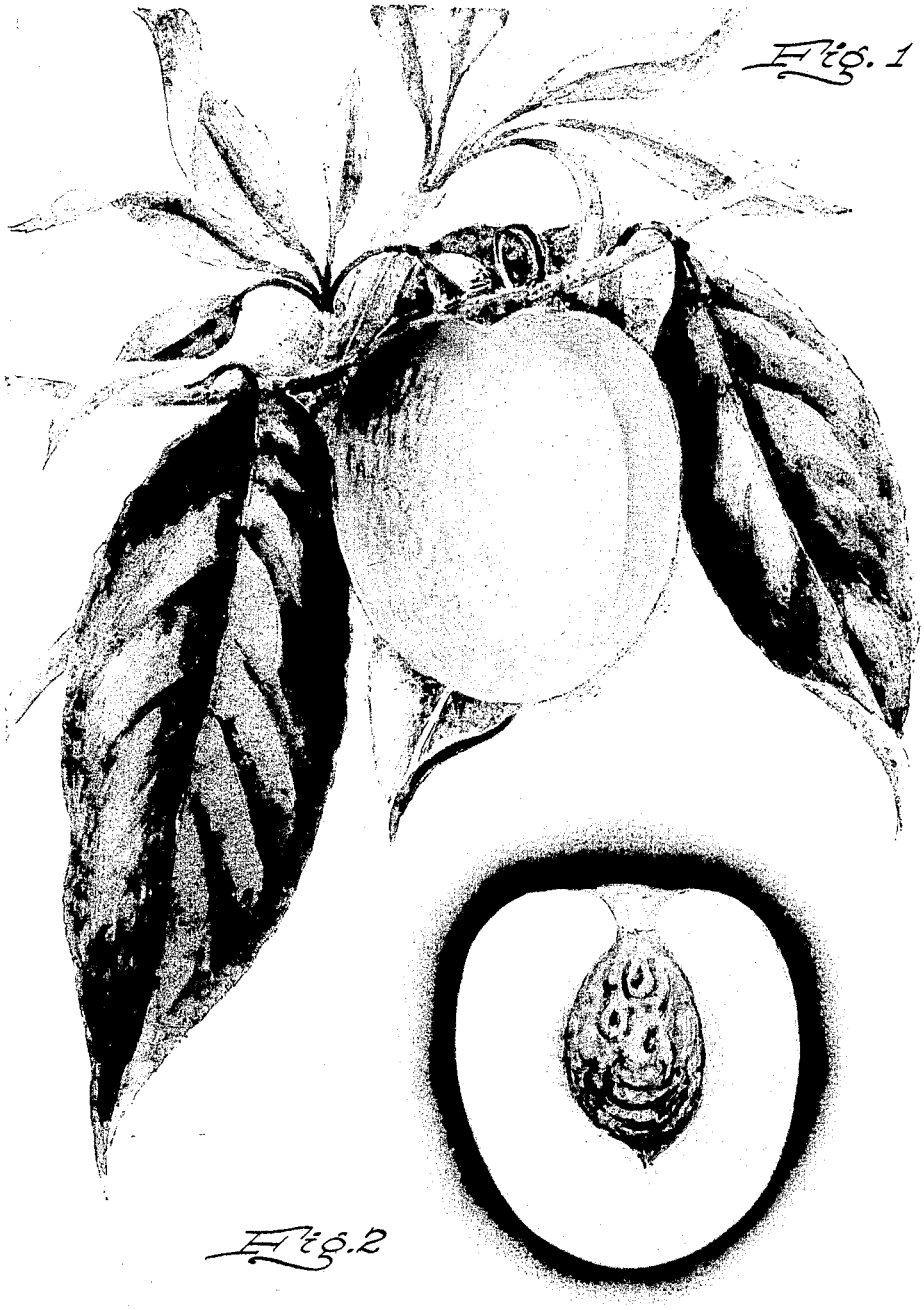
WITNESS
Addison E. Avery
INVENTOR
Harold D. Dougherty
Webster & Webster
ATTYS.

United States Patent Office

Plant Pat. 1,753
Patented Sept. 23, 1958

1,753

NECTARINE TREE

Harold D. Dougherty, Farmersville, Calif.

Application January 14, 1958, Serial No. 708,962

1 Claim. (Cl. 47—62)

The present invention is directed to a new and distinct variety of nectarine tree which bears yellow fleshed, freestone fruit having a rather pale yellow skin, partially overspread by a red blush.

The fruit of the instant variety of nectarine tree is of relatively uniform size, good commercial quality for dessert use, ships well, is above average in keeping quality, and has a favorable harvest period; the fruit being very tasty, as its flesh bears a distinct resemblance to the Elberta peach in flavor.

As the present variety of nectarine has a harvest period substantially with the Sun Grand nectarine, and as both bear freestone fruit, such Sun Grand nectarine has been selected for the purpose of comparison, as follows:

| The Claimed Variety | The Sun Grand Nectarine Tree |
|---|---|
| Medium to dark green foliage | Darker green foliage. |
| Reniform glands | Globose glands. |
| Very large pink blossoms | Relatively small pink blossoms. |
| Medium but more uniform sized fruit. | Larger maximum, but not as uniform sized fruit. |
| Elongated fruit | Round fruit, with a more subdued pistil point. |
| Pale yellow ground color of skin, partially overspread by a red blush. | Medium yellow ground color of skin, frequently entirely overspread with a red blush. |

The present variety of nectarine tree was originated by me on my cultivated ranch located near Farmersville, Tulare County, California; the variety being a first generation Elberta peach seedling crossed with a second generation Le Grand nectarine seedling. When such cross grew to maturity I determined—by careful and continuing observation—that it bore fruit of good commercial grade, and I therefore asexually reproduced the variety by scion wood grafted on a peach seedling growing on my ranch. This reproduction and others have now come into full bearing and are found to carry forward each and every characteristic of the parent tree.

In the drawings:

Fig. 1 is an elevation of one of the fruit, together with a twig and leaves.

Fig. 2 is a sectional elevation of one of the fruit detached, with the stone exposed.

Referring now more particularly to the pomological details of this new and distinct variety of nectarine tree, the following is an outline description thereof; all major color plate identifications being by reference to Maerz and Paul Dictionary of Color:

Tree:
- *Size.*—Medium.
- *Vigor.*—Medium.
- *Growth.*—Spreading.
- *Density.*—Open.
- *Shape.*—Vase formed.
- *Hardiness.*—Hardy.
- *Production.*—Productive
- *Bearing.*—Regular bearer.

Trunk:
- *Size.*—Medium.
- *Texture.*—Medium.

Branches:
- *Size.*—Medium.
- *Texture.*—Smooth.
- *Color.*—Gray-green.
- *Lenticels.*—Medium number; medium size.

Leaves:
- *Size.*—Average — medium. Average length — 5" (maximum length—9"). Average width—1⅛" (maximum width—1¾").
- *Shape.*—Oblanceolate—lanceolate; acutely pointed.
- *Thickness.*—Medium.
- *Texture.*—Smooth.
- *Margin.*—Glandular; crenate.
- *Petiole.*—Medium length; medium thickness.
- *Glands.*—Average number—three (3). Alternate; large; reniform; reddish cast. Positioned on base of leaf.
- *Stipules.*—Two at base of each leaf stalk.
- *Color.*—New leaves: light green (19–L–7). Mature leaves: top side—medium green (23–L–3), shading to somewhat darker green; under side—lighter medium green (22–K–1).

Flower Buds:
- *Hardiness.*—Hardy.
- *Size.*—Large.
- *Length.*—Medium.
- *Shape.*—Conic; pointed.

Flowers:
- *Blooming period.*—First bloom about March 5th, and full bloom about March 10th, in average season. Medium blooming period compared with other varieties.
- *Size.*—Large.
- *Color.*—Pink.

Fruit:
- *Maturity when described.*—Eating ripe.
- *Date of first picking in average season.*—July 7th.
- *Date of last picking in average season.*—July 17th.
- *Size.*—Medium—comparatively uniform. Average diameter axially—2¼". Average transversely in suture plane—3½".
- *Form.*—Symmetrical; narrowly ovoid.
- *Suture.*—Shallow, extends from base to apex, with slight depression beyond pistil point.
- *Ventral surface.*—Rounded; lips equal to unequal.
- *Cavity.*—Rounded; circular. Average depth—⅜". Average breadth—1". Markings—red.
- *Base.*—Truncate.
- *Apex.*—Moderately prolonged.
- *Pistil point.*—Apical.

Skin:
- *Thickness.*—Medium.
- *Texture.*—Medium; tenacious to flesh.
- *Tendency to crack.*—Slight.
- *Down.*—Wanting.
- *Color.*—Pale yellow ground color (9–L–4, shading to 9–L–7), partially overspread and somewhat mottled with red (2–L–10, shading to 6–L–6).

Flesh:
- *Amygdalin.*—Wanting.
- *Juice.*—Moderate.
- *Texture.*—Medium; meaty.
- *Fibers.*—Few; tender.
- *Ripens.*—Comparatively even, but earliest at the apex.
- *Flavor.*—Mild; distinct resemblance to the Elberta peach.
- *Aroma.*—Pronounced.

*Color.* — Flesh color: yellow (9–L–4, shading through 9–A–7 to 9–L–8). Surface of pit cavity: red (3–L–8), with white fibers.

Stone:

*Type.*—Free; parts from flesh smoothly.
*Fibers.*—Medium length.
*Size.*—Medium. Average length—1½". Average breadth—1" to 1⅛". Average thickness—¾".
*Form.*—Oblong.
*Base.*—Oblique.
*Hilum.*—Narrow; oblong.
*Apex.*—Acute.
*Sides.*—Unequal; curved on right and left.
*Surface.*—Regularly furrowed toward apex; pitted toward base.
*Ridges.*—Rounded toward apex; interrupted.
*Pits.*—Elongated.
*Ventral edge.*—Thick, with slight wing toward base.
*Dorsal edge.*—Narrow, with shallow groove toward base.
*Tendency to split.*—Slight.
*Color.*—Reddish brown (purple cast), (5–E–6), shading to a stronger brown (7–L–11).

Use: Local; dessert.
Keeping quality: Very good.
Shipping quality: Good.

Of the previous existing varieties hereinbefore mentioned the Le Grand nectarine and the Sun Grand nectarine are the subject of United States plant patents, Nos. 549 and 974, respectively; the Elberta peach being unpatented.

The tree and its fruit herein described may vary in slight detail due to climatic and soil conditions under which the variety may be grown.

The following is claimed:

A new and distinct variety of nectarine tree, as illustrated and described, characterized by medium sized, yellow fleshed, freestone fruit having a flavor resembling the Elberta peach, and skin of yellow ground color, partially overspread with red; and further characterized—in comparison with the Sun Grand nectarine—by substantially the same harvest period, medium to dark green mature foliage but not as deep a shade, reniform rather than globose glands, larger size blossoms, and fruit more uniform in size and elongated rather than round.

No references cited.